United States Patent
De Mesanstourne et al.

(10) Patent No.: US 6,410,593 B1
(45) Date of Patent: Jun. 25, 2002

(54) ANTIDANDRUFF COMPOSITIONS

(75) Inventors: Régine De Mesanstourne, Maisons-Lafitte; Hélène Lebon, Louveciennes; Hélène Le Gall, Viry Chatillon, all of (FR)

(73) Assignee: CECA S.A., Puteaux (FR)

( * ) Notice: Subject to any disclaimer, the term of this patent is extended or adjusted under 35 U.S.C. 154(b) by 0 days.

(21) Appl. No.: 09/775,602

(22) Filed: Feb. 5, 2001

Related U.S. Application Data

(63) Continuation of application No. 09/249,310, filed on Feb. 12, 1999, now abandoned.

(30) Foreign Application Priority Data

Feb. 13, 1998 (FR) .............................. 98 01771

(51) Int. Cl.⁷ ............................................ A61K 31/205
(52) U.S. Cl. ....................................... 514/556; 514/881
(58) Field of Search .......................................... 514/556

(56) References Cited

U.S. PATENT DOCUMENTS 4,166,845 A    9/1979    Hansen et al.

FOREIGN PATENT DOCUMENTS

| | | |
|---|---|---|
| EP | 0 799 612 A2 | 10/1997 |
| JP | 02-067212 | 3/1990 |
| WO | WO 93/18737 | 9/1993 |

*Primary Examiner*—Rebecca Cook
(74) *Attorney, Agent, or Firm*—Smith, Gambrell & Russell, LLP

(57) ABSTRACT

Aqueous shampoo compositions whose washing base consists of an anionic surfactant and an amphoteric surfactant, in which some of the amphoteric agent consists of undecylenamidopropylbetaine, are described. This amphoteric principle gives these compositions effective antifungal properties against the action of *Pityrosporum ovalae* and constitutes a treatment for reducing the formation of dandruff.

13 Claims, No Drawings

ANTIDANDRUFF COMPOSITIONS

This is a continuation of 09/249,310 filed Feb. 12, 1999, abandoned

FIELD OF THE INVENTION

The present invention relates to novel compositions which are useful in cosmetology, in particular shampoos and foaming gels, which are intended to care for the hair and/or the scalp, in particular to combat dandruff or to prevent its formation. The invention is directed towards shampoos whose washing base contains an amphoteric surfactant and an anionic surfactant, where appropriate supplemented with a thickener and/or a hair conditioner.

BACKGROUND OF THE INVENTION

In shampoos whose washing base contains an anionic surfactant and an amphoteric surfactant, the washing function itself is based on the two components, but a foaming function is provided by the amphoteric surfactant. In very general terms, the amphoteric surfactant is an alkylbetaine, in particular a lauric-, coconut- or palm kernel-based alkylamidopropylbetaine. The mechanical elimination of dandruff, the causative agent of which is a fungus, *Pityrosporum ovalae*, is one of the expected results of shampooing, but it has also been sought to develop shampoos which combat or prevent the formation of dandruff. For this, use has been made of various antifungal agents.

Among the standard antifungal agents, mention may be made of:

preserving agents whose fungal spectrum is oriented towards fungi and particularly yeasts, such as sorbic acid and dehydroacetic acid, active agents listed as anti-yeast agents, such as zinc pyrithione, piroctone-olamine and climbazole, a few surfactants derived from undecylenic acid, in particular 4-sulpho-{2-[(1-oxo-10-undecenyl)amino] ethyl}butanedioic ester, disodium (RN=26650-05-5) (or disodium undecylenamido MEA sulphosuccinate, according to the CTFA name adopted in the International Cosmetic Ingredient Dictionary, 6th edition, by The Cosmetics, Toiletry and Fragrance Association, 1995), and N-(2-hydroxyethyl)undecenamide (RN= 20545-92-0 and 40839-40-5) (CTFA : undecylenamide MEA).

However, some antifungal active principles among those most commonly used show cytotoxic potential in vitro. It is necessary to lower the working amounts thereof to below an acceptable cytotoxicity threshold, or even to combine them with molecules which protect the integrity of skin cells which are damaged or inflamed to a greater or lesser extent. These products have other drawbacks: for example, piroctone-olamine poses coloration problems in shampoos containing this active principle, zinc pyrithione is a water-insoluble powder which leads to opaque formulations that are unstable in light, climbazole is water-insoluble and requires the mandatory use of solvents (ethanol, benzyl alcohol).

As regards the undecylenic acid derivatives, some have already been cited for their antibacterial and antifungal activity, in particular the zinc salts of undecylenamido MEA sulphosuccinate (WO 97/18823 of 29.05.97 from Pièrre Fabre; EP 23676 of 11.02.81 from Rewo) and of tricarboxylic acid which are derived from the product of the Diels-Alder reaction between maleic anhydride and undecylenic acid (EP 71025 of 9.02.83 from Grillo Werke AG), as well as a number of esters (JP 08/053,326 of 27.02.96 from Kanebo; EP 28459 of 13.05.81 from Imperial Chemical Industries Ltd.). As examples, among the most common undecylenic acid derivatives are found N-(2-hydroxyethyl) undecenamide (CTFA : undecylenamide MEA) and 4-sulpho-{2-[(1-oxo-10-undecenyl)amino] ethyl}butanedioic ester, disodium (CTFA: disodium undecylenamido MEA sulphosuccinate), which are sold, respectively, under the trade names "Rewocid®U185 or Witcamide®6570" and "Rewocid®SB U185" by the company Witco. However, these derivatives are not amphoteric.

It has been discovered, unexpectedly, that in addition to the usual characteristics of betaines (co-surfactant, good foaming power, mild detergent), N-(carboxymethyl)-N,N-dimethyl-3-[(1-oxoundecenyl)amino]-1-propanaminium hydroxide (RN=98510-75-9, neutral zwitterionic form) or CTFA: undecylenamidopropylbetaine

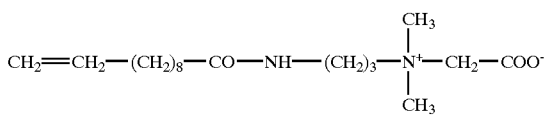

has antifungal activity towards *Pityrosporum ovalae* and thus develops antidandruff efficacy which has never been cited to date. Consequently, it offers the very great advantage of being able to constitute an amphoteric component of a shampoo which itself has the desired antidandruff properties. This discovery is exploited in shampoos of the invention, which are essentially aqueous compositions of a washing base consisting of amphoteric surfactants and anionic surfactants and whose amphoteric surfactants do themselves—and this is the characteristic of the invention—partly consist of undecylenamidopropylbetaine.

For the purposes of the invention, the term anionic surfactant is understood to refer to one or more compounds taken from the group formed of ($C_{10}$ to $C_{14}$)alkyl sulphates and ($C_{10}$ to $C_{14}$)alkyl ether sulphates. Lauryl ether sulphates are anionic surfactants used commonly by shampoo formulators.

For the purposes of the invention, the term amphoteric surfactant is understood to refer to the compounds chosen, alone or as a mixture, from alkyl amphocarboxyglycinates, alkyl amphocarboxypropionates, alkyl amphodiacetates, alkyl amphodipropionates, alkyl amphoglycinates, alkyl amphopropionates, alkyl iminopropionates, alkyl iminodipropionates, alkyl amphopropylsulphonates, alkylbetaines, alkylamidopropylbetaines, alkylsultaines and alkylamidopropylhydroxysultaines. In this list, alkyl is understood in the sense of $C_{10}$ to $C_{14}$ hydrocarbon-based chains and more especially lauric, coconut or palm kernel fatty acid residues or equivalent sources. Cocoamidopropylbetaines are amphoteric compounds that are preferred for preparing the formulations according to the invention.

Undecylenamidopropylbetaine, which is the characteristic amphoteric compound of the invention, is an undecylenic-based alkylamidopropylbetaine. It can be prepared according to processes known to those skilled in the art, in particular by following the procedure described in U.S. Pat. No. 3,225,074 (American Cyanamid) which consists in reacting undecylenic acid with N,N-dimethyl-1,3-propanediamine (DMAPA) between 140 and 200° C., followed by reacting the tertiary amidoamine

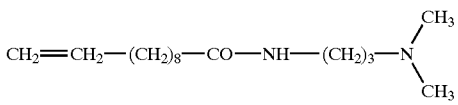

thus obtained with monochloroacetic acid in the presence of an alkaline salt or the corresponding salt of this acid, the reaction being carried out in aqueous medium. The alkali metal chloride, usually sodium chloride, co-produced during the reaction is generally left in this aqueous betaine solution.

The compositions of the invention are aqueous solutions in which the content of all of the constituents of the washing base (amphoteric and anionic compounds) lies within certain limits so as to ensure their physical equilibrium, in particular their homogeneity and their transparency (in the absence of the intentional introduction of pearlescent agents), these limits naturally being capable of varying to a certain extent depending on the individual components used, which will be represented by the following symbols: An used for anionic components, Amph for amphoteric compounds, $\Sigma$Amph representing all of the amphoteric compounds, AmphU representing undecylenic betaine, Amph* representing the amphoteric components except for undecylenic betaine.

This gives, on the one hand, as regards the anionic components/amphoteric compounds equilibrium:

12.5% $\leq$ An+$\Sigma$Amph $\leq$ 17.6
5% $\leq$ An $\leq$ 15
3.5% $\leq$ $\Sigma$Amph $\leq$ 9.2 on the other hand, as regards the amphoteric compounds/undecylenic amphoteric component equilibrium:

3.5% $\leq$ $\Sigma$Amph $\leq$ 9.2
2% $\leq$ Amph* $\leq$ 7
1.5% $\leq$ AmphU $\leq$ 3.5

A common shampoo composition according to the invention will have, for example, the general composition

| | |
|---|---|
| Sodium lauryl ether sulphate | 5 to 15% |
| Cocoamidopropylbetaine | 2 to 7% |
| Undecylenamidopropylbetaine | 1.5 to 3.5% |
| Ordinary ingredients of shampoo formulations and demineralized water | qs 100% |

The common ingredients in the formulation of products of this type form part of these compositions, namely:

thickeners intended to give the shampoos a sufficient consistency and improved cosmetic qualities. Among the known thickeners, carbomers (acrylic acid homopolymers crosslinked with an allylic ether of pentaerythritol, of sucrose or of propylene), PEG esters, laurylpyrrolidone, acrylic copolymers and cationic polymers of natural or synthetic origin, including certain polyquaternium compounds (see the conditioners below) give very satisfactory results in the application considered, in particular bearing in mind that viscosities of greater than 1000 mPa.s, preferably between 1000 mPa.s and 30,000 mPa.s, could be obtained with these specific products ("Carbopol Ultrez®10" from BF Goodrich, "Atlas®G-1821" from ICI, "Surfadone®LP 300" from ISP, "Acrysol®22" from Rohm & Haas, "Jaguar®C 162" and "Rhodicare®T" from Rhône-Poulenc, "Ucare®Polymer Jr. 400" from Amerchol, "Mackernium®7" from Jan Dekker/MacIntyre and "Gafquat®755 N" from ISP). These specific thickeners make it possible to obtain acceptable viscosities when they are used at concentrations of between 0 and 4% by weight relative to the whole composition, preferably between 0.2 and 2% by weight.

Conditioners, these being products intended to improve the cosmetic properties of detergent solution, generally cationic or amphoteric polymers, oils, and in particular silicones or silicone derivatives, the compatibility of which with all of the other constituents of the formulation should be checked, and in particular in order to avoid the formation of cosmetically unacceptable cloudy gels; in this respect, it has been found that the use of cationic polymers such as polyquaternium-7 (in particular "Mackernium 7" from Jan Dekker/MacIntrye), polyquaternium-10 (in particular "Ucare Polymer JR 400" from Amerchol) and polyquaternium-11 (in particular "Gafquat 755 N" from ISP) at concentrations of about 1 to 4%, allow entirely clear gels to be conserved.

Foam enhancers/stabilizers, these being compounds taken from the group consisting of diethanolamine alkanolamide or tertiary amine oxides, which can be used at contents of between 1 and 5% by weight relative to the total weight of the composition, but which are increasingly tending to be left out of the formulation for fear of the toxicity induced by some of their possible impurities.

The compositions can also contain certain adjuvants that are common in the shampoo sector, preserving agents, sequestering agents, softeners, foam modifiers, dyes, pearlescent agents, moisturizers, antiseborrhoeic agents, vitamins, sunscreens and fragrances. As regards the fragrances in the formulation, it should be pointed out that the low characteristic odour of undecenylamidopropylbetaine permits any fragrance, from the most discreet to the most specific.

The use, alone or as a mixture, of common preserving agents such as phenoxyethanol, methylparaben, ethylparaben, propylparaben and butylparaben (CTFA nomenclatures, INCI, 6th edition) at concentrations of between 0.25% and 1% by weight relative to the whole composition, has proven to be particularly useful for obtaining effective and long-lasting protection of foaming gels.

The compositions according to the invention can also contain additional solvents, for example glycols or glycerol, which, at concentrations of between 2% and 8% by weight, and even more particularly between 4% and 6% by weight, relative to the whole composition, improve the physical stability of the formulations at low temperatures (problems of clouding or of crystal growth in particular) and promote rapid penetration of the active principle into the horny layer and improve the condition of irritated horny layer (hydration of the surface epidermal layers of the scalp).

The pH of these compositions must be between 4.5 and 7.0, especially around 6, in order for the antifungal activity to be preserved at the optimum level. Adjustment of the pH to the desired value is conventionally carried out by addition of an organic or inorganic acid or base, for example citric acid, succinic acid, phosphoric acid, sodium hydroxide or sodium carbonate.

The washing and antifungal compositions according to the invention are stable (absence of decantation or of demixing of phases) and homogeneous over time within a temperature range between 4 and 45° C., both in natural light and under our Sun Test ageing conditions. They are well tolerated by the skin. They also have good foaming and washing power, which allows the removal of dandruff and good rinsability. Their viscosity must be sufficient for them to be easy to measure out in the hand. In practice, their viscosity must be greater than 1000 mPa.s The formulations according to the invention can be used for the preparation of more or less viscous, very faintly coloured transparent products of liquid or gel texture.

The gel forms are preferred for the curative, topical-route treatment of dandruff, these forms being used as shampoos, i.e. they are applied to the skin, the hair and/or the scalp for a few minutes, and then rinsed with water.

Concrete examples of formulations will illustrate the invention.

EXAMPLES

The compositions described below are expressed as weight percentages of active materials. The weight percentages of the crude products or of the corresponding commercial products used have been specified.

The undecylenamidopropylbetaine used in these examples was synthesized according to the procedure described above. Its composition is established as follows:

| | |
|---|---|
| Undecylenamidopropylbetaine | 30.0 ± 2% |
| NaCl | 6% max. |
| Undecylenic acid | 0.5% max. |
| Amidoamine | 0.5% max. |
| Sodium monochloroacetate | <20 ppm |

Its pH at 5% in water is from 5.8 to 7.5 and its Hazen colour is less than 300.

Example 1

Compared Efficacy of Undecylenamidopropylbetaine and Octopyrox

The antidandruff and seboregulatory efficacy tests were carried out over a period of 15 days, on a Test Panel of 20 individuals whose demographic characteristics are as follows:

| Age | Number | Average | Standard deviation | Minimum age | Maximum age |
|---|---|---|---|---|---|
| Total | 20 | 30 | 9 | 23 | 28 | a) Antidandruff Action

Undecylenamidopropylbetaine (Amphoram®U from CECA S.A.) was compared with piroctone olamine (CFTA) or 1-hydroxy-4-methyl-6-(2,4,4-trimethylpentyl)-2(1H) pyridone; ethanol (1:1) salt (RN=68890-66-4), taken in its commercial form as Octopyrox® (Hoechst), at the minimum inhibitory doses (M.I.C.) for *Pityrosporum ovalae*, i.e., respectively, 2% and 0.2% beforehand. The results of this comparative study, expressed as a percentage of variations on D15 relative to D1, are presented in the following table:

| | Area occupied by dandruff | | Dandruff removal index | |
|---|---|---|---|---|
| Products | Amphoram U | Octopyrox | Amphoram U | Octopyrox |
| Results | −29 | −7 | −36 | −5 | b) Sebumetry Results

The results of the sebumetry index, measured with the sebumeter sold by the company Courage-Khazka, expressed as a percentage of variation on D15 relative to D1, are presented in the following table:

| | Sebumetry index | |
|---|---|---|
| Products | Amphoram U | Octopyrox |
| Results | −7 | −4 |

From this set of results, it is concluded:

that the state of dandruff of the 20 individuals was improved (about 30 to 40% decrease in the area occupied and increase in the dandruff removal index) with Amphoram U whereas it remained stable with Octopyrox;

that the sebumetry level did not vary significantly, irrespective of the product used, which demonstrates the absence of irritation.

No side effects were recorded, irrespective of the product used.

Example 2

Transparent, Viscous Antidandruff Shampoo

| | |
|---|---|
| Sodium lauryl ether sulphate[1] | 8.4 |
| Cocoamidopropylbetaine[2] | 3.0 |
| Undecylenamidopropylbetaine[3] | 2.0 |
| Diethanolamine laurylamide[4] | 2.0 |
| Preserving agent, fragrance | qs |
| Citric acid | qs |
| Demineralized water | qs 100 |

Commercial products used
[1]Empicol ® ESB 3M (Albright & Wilson) for 28%
[2]Amphoram ® C 30 (CECA) for 10%
[3]Amphoram ® U (CECA) 6.6%
[4]Mackamide ® LMD (MacIntyre) for 2%

Characteristics

Viscous shampoo (viscosity, measured with a Brookfield R5 V10 viscometer, of 12,800 mPa.s), flows well from a bottle, spreads well on the hair, totally transparent and colourless (colour=40 Hazen), pH=6.6.

Stable formulation, tested at +4° C. and +45° C. (exposure for 1 month to natural light behind glass, 310 nm) and Suntest (15 days of accelerated ageing in Suntest-type apparatus, power 500 watt/m$^2$, 300 to 800 nm);

Forms an excellent, stable, copious white foam which is easy to rinse out.

Example 3

Transparent and Very Viscous Antidandruff Shampoo for Stubborn Dandruff

| | |
|---|---|
| Sodium lauryl ether sulphate[1] | 8.4 |
| Cocoamidopropylbetaine[2] | 4.5 |
| Undecylenamidopropylbetaine[3] | 3.0 |
| Diethanolamine laurylamide[4] | 2.0 |
| Preserving agent, fragrance | qs |
| Citric acid | qs |
| Demineralized water | qs 100 |

Commercial products used

-continued (1)Empicol ® ESB 3M (Albright & Wilson) for 28%
(2)Amphoram ® C 30 (CECA) for 15%
(3)Amphoram ® U (CECA) 9.9%
(4)Mackamide ® LMD (MacIntyre) for 2%

Characteristics

Very viscous shampoo (viscosity, measured with a Brookfield R5 V10 viscometer, of 31,000 mPa.s)

Totally transparent and colourless (colour: 60 Hazen).

pH : 6.1.

Stable formulation, tested at +4° C. and 45° C. (1 month) and Suntest (15 h).

Forms an excellent, stable, copious white foam which is easy to rinse out.

Example 4

Transparent, Low-viscosity Antidruff Shampoo Shampoo

| | |
|---|---|
| Sodium lauryl ether sulphate(1) | 7.5 |
| Cocoamidopropylbetaine(2) | 3.0 |
| Undecylenamidopropylbetaine(3) | 2.0 |
| Preserving agent, fragrance | qs |
| Sodium chloride | 1.0 |
| Demineralized water | qs 100 |

Commercial products used
(1)Empicol ® ESB 3M (Albright & Wilson) for 25%
(2)Amphoram ® C 30 (CECA) for 6.6%
(3)Amphoram ® U (CECA) 9.9%

Characteristics

Totally transparent and colourless fluid shampoo

Flows well from a bottle, spreads well on the hair

Excellent, stable, copious white foam, which is easy to rinse out

Stable formulation, tested at +4° C. and +45° C. (1 month in natural light) and Suntest (15 h 00 in the Suntest)

pH : 6.2

Viscosity (Brookfield R5 V100): 1040 mPa.s

Colour: 129 Hazen

Example 5

Transparent, Viscous Antidandruff Shampoo

| | |
|---|---|
| Sodium lauryl ether sulphate(1) | 8.4 |
| Cocoamidopropylbetaine(2) | 4.5 |
| Undecylenamidopropylbetaine(3) | 2.0 |
| Sodium chloride | 0.5 |
| Preserving agent, fragrance | qs |
| Demineralized water | qs 100 |

Commercial products used
(1)Empicol ® ESB 3M (Albright & Wilson) for 28%
(2)Amphoram ® C 30 (CECA) for 15%
(3)Amphoram ® U (CECA) 6.6%

Characteristics

Totally transparent and colourless viscous shampoo

Flows well from a bottle, spreads well on the hair

Excellent, stable, copious white foam, which is easy to rinse out

Stable formulation, tested at +4° C. and +45° C. (1 month in natural light) and Suntest (15 h 00 in the Suntest)

pH : 6.2

Viscosity (Brookfield R5 V10): 10,600 mPa.s

Colour: 88 Hazen

Example 6

Transparent, Low-viscosity Antidandruff Shampoo

| | |
|---|---|
| Sodium lauryl ether sulphate(1) | 6.3 |
| Cocoamidopropylbetaine(2) | 6.3 |
| Undecylenamidopropylbetaine(3) | 2.0 |
| Preserving agent, fragrance | qs |
| Demineralized water | qs 100 |

Commercial products used
(1)Empicol ® ESB 3M (Albright & Wilson) for 25%
(2)Amphoram ® C 30 (CECA) for 15%
(3)Amphoram ® U (CECA) 6.6%

Characteristics

Transparent and colourless fluid shampoo

Flows well from the bottle, spreads well on the hair

Excellent, stable, copious white foam, which is easy to rinse out

Stable formulation, tested at +4° C. and +45° C. (1 month in natural light) and Suntest (15 h 00 in the Suntest)

pH : 6.0

Viscosity (Brookfield R5 V100): 2300 mPa.s

Colour: 50 Hazen

Example 7

Opaque, Gelled, Viscous Antidandruff Shampoo

| | |
|---|---|
| Sodium lauryl ether sulphate(1) | 7.5 |
| Cocoamidopropylbetaine(2) | 4.5 |
| Undecylenamidopropylbetaine(3) | 2.0 |
| Carbomer(5) | 0.9 |
| 99% triethanolamine | 1.0 |
| Preserving agent, fragrance | qs |
| Demineralized water | qs 100 |

Commercial products used
(1)Empicol ® ESB 3M (Albright & Wilson) for 25%
(2)Amphoram ® C 30 (CECA) for 15%
(3)Amphoram ® U (CECA) 6.6%
(5)Carbopol Ultrez ® 1.0%

Characteristics

Opaque viscous shampoo

Flows well from the bottle, spreads well on the hair

Excellent, stable, copious white foam, which is easy to rinse out

Stable formulation, tested at +4° C. and +45° C. (1 month in natural light) and Suntest (15 h 00 in the Suntest)

pH : 5.1

Viscosity (Brookfield R5 V10): 10,500 mPa.s

Example 8

Pearlescent, White, Silky Antidandruff Shampoo

| | |
|---|---|
| Sodium lauryl ether sulphate(1) | 7.5 |
| Cocoamidopropylbetaine(2) | 4.5 |

-continued

| | |
|---|---|
| Undecylenamidopropylbetaine[3] | 2.0 |
| Carbomer[5] | 0.9 |
| Glycol stearate[6] | 2.0 |
| 99% triethanolamine | 1.0 |
| Preserving agent, fragrance | qs |
| Demineralized water | qs 100 |

Commercial products used
[1] Empicol ® ESB 3M (Albright & Wilson) for 25%
[2] Amphoram ® C 30 (CECA) for 15%
[3] Amphoram ® U (CECA) 6.6%
[5] Carbopol Ultrez ® 1.0%
[6] Cutina ® AGS, 2.0%

Characteristics

Pearlescent white shampoo, beautiful, rich, milky and viscous appearance

Flows well from the bottle, spreads well on the hair

Excellent, dense white foam, which is easy to rinse out

Stable formulation, tested at +4° C. and +45° C. (1 month in natural light) and Suntest (15 h 00 in the Suntest)

pH : 5.1

Viscosity (Brookfield R5 V10): 20,000 mPa.s

Example 9

Fluid, Transparent, Gelled Antidandruff Shampoo

| | |
|---|---|
| Sodium lauryl ether sulphate[1] | 7.5 |
| Cocoamidopropylbetaine[2] | 3.0 |
| Undecylenamidopropylbetaine[3] | 2.0 |
| Copolymer of acrylic acid and of $C_{20}$ fatty alkyl acrylate[7] | 0.6 |
| Sodium hydroxide | 0.1 |
| Preserving agent, fragrance | qs |
| Demineralized water | qs 100 |

Commercial products used
[1] Empicol ® ESB 3M (Albright & Wilson) for 25%
[2] Amphoram ® C 30 (CECA) for 10%
[3] Amphoram ® U (CECA) 6.6%
[7] Acrysol ® 22 for 2.0%

Characteristics:

Translucent fluid shampoo

Flows well from the bottle, spreads well on the hair

Excellent, stable, copious white foam, easy to rinse out

Stable formulation, tested at +4° C. and +45° C. (1 month in natural light) and Suntest (15 h 00 in the Suntest)

pH : 6.5

Viscosity (Brookfield R5 V50): 3700 mPa.s

Colour: 204 Hazen

Example 10

Transparent, Low-viscosity Antidandruff Shampoo

| | |
|---|---|
| Sodium lauryl ether sulphate[1] | 7.5 |
| Cocoamidopropylbetaine[2] | 3.0 |
| Undecylenamidopropylbetaine[3] | 2.0 |
| Polyquaternium-10[8] | 2.0 |
| Preserving agent, fragrance | qs |
| Demineralized water | qs 100 |

Commercial products used
[1] Empicol ® ESB 3M (Albright & Wilson) for 25%
[2] Amphoram ® C 30 (CECA) for 10%
[3] Amphoram ® U (CECA) 6.6%
[8] Ucare ® Polymer JR 400 for 2.0%

Characteristics:

Translucent fluid shampoo

Flows well from the bottle, spreads well on the hair

Excellent, stable, copious white foam, easy to rinse out

Stable formulation, tested at +4° C. and +45° C. (1 month in natural light) and Suntest (15 h 00 in the Suntest)

pH : 6.2

Viscosity (Brookfield R5 V100): 1880 mPa.s

Colour: 78 Hazen

Example 11

Transparent, Low-viscosity, Gentle Antidandruff Shampoo (8/2=HB 1.122 A)

| | |
|---|---|
| Sodium lauryl ether sulphate[1] | 12.0 |
| Cocoamidopropylbetaine[2] | 3.6 |
| Undecylenamidopropylbetaine[3] | 2.0 |
| Polyquaternium-7[9] | 0.3–0.4 |
| Preserving agent, fragrance | qs |
| Demineralized water | qs 100 |

Commercial products used
[1] Empicol ® ESB 3M (Albright & Wilson) for 40%
[2] Amphoram ® C 30 (CECA) for 12%
[3] Amphoram ® U (CECA) 6.6%
[9] Mackernium ® 7 for 4.0%

Characteristics:

Transparent, colourless fluid shampoo

Flows well from the bottle, spreads well on the hair

Excellent soft foam, easy to rinse out

Stable formulation, tested at +4° C. and +45° C. (1 month in natural light) and Suntest (15 h 00 in the Suntest)

pH : 6.7

Viscosity (Brookfield R5 V100): 1400 mPa.s

Colour: 44 Hazen

Example 12

Very Gentle Pearlescent White Antidandruff Shampoo for Frequent Use

| | |
|---|---|
| Sodium lauryl ether sulphate[1] | 9.0 |
| Cocoamidopropylbetaine[2] | 2.4 |
| Undecylenamidopropylbetaine[3] | 2.0 |
| Sodium methylcocoyl taurate[10] | 3.0 |
| Glycol distearate[6] | 2.0 |
| Polyquaternium-11[11] | 0.4 |
| Laurylpyrrolidone[12] | 2.0 |
| Preserving agent, fragrance | qs |
| Demineralized water | qs 100 |

Commercial products used

-continued (1)Empicol ® ESB 3M (Albright & Wilson) for 30%
(2)Amphoram ® C 30 (CECA) for 8.0%
(3)Amphoram ® U (CECA) 6.6%
(9)Mackernium ® 7 for 4.0%
(10)Cutina ® AGS 2.0%
(11)Gafquat ® 755 N for 2.0%
(12)Surfadone ® LP 300 for 2.0%

Characteristics:

Pearlescent white viscous shampoo

Pours well from the bottle, spreads well on the hair

Excellent white foam, easy to rinse out

Stable formulation, tested at +4° C. and +45° C. (1 month in natural light) and Suntest (15 h 00 in the Suntest)

pH : 6.6

Viscosity (Brookfield R5 V10): 18,300 mPa.s

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. An aqueous antifungal and antidandruff shampoo composition with a washing base comprising:

an anionic surfactant comprising one or more compounds selected from the group consisting of ($C_{10}$ to $C_{14}$) alkyl sulfates, and ($C_{10}$ to $C_{14}$) alkyl ether sulphates or a mixture thereof;

an amphoteric surfactant comprising one or more compounds selected from the group consisting of alkyl amphocarboxyglycinates, alkyl amphocarboxypropionates, alkyl amphodiacetates, alkyl amphodipropionates, alkyl amphoglycinates, alkyl amphopropionates, alkyl iminopropionates, alkyl iminodipropionates, alkyl amphopropyl sulphonates, alkylbetaines, alkylamidopropylbetaines, alkylsultaines, and alkylamidopropylhydroxysultaines or a mixture thereof; and a single antifungal agent for providing antifungal activity toward *Pityrosporum ovalae* and antidandruff efficacy, said antifungal agent consisting of undecylenamidopropylbetaine; wherein said undecylenamidopropylbetaine is in an amount as a percent by weight of the aqueous shampoo composition of less than the total of said anionic surfactant plus said amphoteric surfactant without said undecylenamidopropylbetaine.

2. The aqueous shampoo composition according to claim 1, wherein said anionic surfactant is a lauryl ether sulphate and said amphoteric surfactant comprises a cocoamidopropylbetaine and said undecylenamidopropylbetaine.

3. The aqueous shampoo composition according to claim 1, further comprising demineralized water, and optional ingredients selected from the group consisting of thickeners, conditioners, foam enhancers/stabilizer, preserving agents, sequestering agents, softeners, foam modifiers, dyes, pearlescent agents, moisturizers, antiseborrhoeic agents, vitamins, sunscreens, fragrances preserving agents and solvents or a mixture thereof.

4. The aqueous shampoo composition according to claim 1 wherein said anionic surfactant is sodium lauryl ether sulphate present in an amount by weight relative to the composition of 5% to 15%, wherein said amphoteric surfactant is cocoamidopropylbetaine present in an amount by weight relative to the composition of 2% to 7% and undecylenamidopropylbetaine present in an amount by weight relative to the composition of 1.5% to 3.3%, and wherein the composition further comprises demineralized water present in an amount by weight relative to the composition of qo 100%.

5. The aqueous shampoo composition according to claim 1, wherein the composition has a pH of between 4.5 and 7.0.

6. An aqueous antifungal and antidandruff shampoo composition with a washing base comprising an anionic surfactant and an amphoteric surfactant, said anionic surfactant comprising one or more compounds selected from the group consisting of ($C_{10}$ to $C_{14}$) alkyl sulfates, and ($C_{10}$ to $C_{14}$) alkyl ether sulphates or a mixture thereof; and said amphoteric surfactant comprising one or more compounds selected from the group consisting of alkyl amphocarboxyglycinates, alkyl amphocarboxypropionates, alkyl amphodiacetates, alkyl amphodipropionates, alkyl amphoglycinates, alkyl amphopropionates, alkyl iminopropionates, alkyl iminodipropionates, alkyl amphopropyl sulphonates, alkylbetaines, alkylamidopropylbetaines, alkylsultaines, and alkylamidopropylhydroxysultaines or a mixture thereof; and wherein said anionic and said amphoteric compounds are distributed, in regard to the anionic compounds/amphoteric compounds equilibrium, as a percent by weight of the aqueous shampoo composition, according to the following inequations:

$12.5\% \leq An + \Sigma Amph \leq 17.6\%$ $5\% \leq An \leq 15\%$ $3.5\% \leq \Sigma Amph \leq 9.2\%$ and in regard to the amphoteric compounds/undecylenic amphoteric component equilibrium, according to the inequations:

$3.5\% \leq \Sigma Amph \leq 9.2\%$ $2\% \leq Amph^* \leq 7\%$ $1.5\% \leq AmphU \leq 3.5\%$ wherein An represents anionic compounds, Amph represents amphoteric compounds, $\Sigma Amph$ represents all of the amphoteric compounds, AmphU represents undecylenamidopropylbetaine, and Amph* represents the amphoteric compounds except for undecylenamidopropylbetaine; and wherein said undecylenamidopropylbetaine has antifungal activity toward *Pityrosporum ovalae* and thereby provides antidandruff efficacy.

7. The aqueous shampoo composition according to claim 6 wherein said anionic surfactant (An) is sodium lauryl ether sulphate, and wherein said amphoteric surfactant (Amph*) is cocoamidopropylbetaine.

8. The aqueous shampoo composition according to claim 6, wherein said anionic surfactant (An) is a lauryl ether sulphate and said amphoteric surfactant ($\Sigma Amph$) comprises a cocoamidopropylbetaine and said undecylenamidopropylbetaine.

9. The aqueous shampoo composition according to claim 6, further comprising demineralized water, and optional ingredients selected from the group consisting of thickeners, conditioners, foam enhancers/stabilizers, preserving agents, sequestering agents, softeners, foam modifiers, dyes, pearlescent agents, moisturizers, antiseborrhoeic agents, vitamins, sunscreens, fragrances preserving agents and solvents or a mixture thereof.

10. The aqueous shampoo composition according to claim 6, wherein the composition has a pH of between 4.5 and 7.0.

11. The aqueous shampoo composition according to claim 6, wherein said undecylenamidopropylbetaine is a sole antifungal agent in the aqueous shampoo composition.

12. A method for the topical treatment of the formation of dandruff duo to the action of *Pityrosporum ovalae* comprising treating an individual in need thereof with the aqueous shampoo composition according to claim 6 in an amount sufficient to treat the formation of dandruff in the individual.

13. A method for the topical treatment of the formation of dandruff due to the action of Pityrosporum ovalae comprising treating an individual in need thereof with an aqueous shampoo composition in an amount sufficient to treat the formation of dandruff in the individual, the aqueous shampoo composition having a washing base comprising:

an anionic surfactant comprising one or more compounds selected from the group consisting of ($C_{10}$ to $C_{14}$) alkyl sulfates, and ($C_{10}$ to $C_{14}$) alkyl ether sulphates or a mixture thereof;

an amphoteric surfactant comprising one or more compounds selected from the group consisting of alkyl amphocarboxyglycinates, alkyl amphocarboxypropionates, alkyl amphodiacetates, alkyl amphodipropionates, alkyl amphoglycinates, alkyl amphopropionates, alkyl iminopropionates, alkyl iminodipropionates, alkyl amphopropyl sulphonates, alkylbetaines, alkylamidopropylbetaines, alkylsultaines, and alkylamidopropylhydroxysultaines or a mixture thereof; and a single antifungal agent for providing antifungal activity toward *Pityrosporum ovalae* and antidandruff efficacy, said antifungal agent consisting of undecylenamidopropylbetaine.

* * * * *